United States Patent
Fujii et al.

(10) Patent No.: US 11,883,683 B2
(45) Date of Patent: Jan. 30, 2024

(54) PARTICLE THERAPY SYSTEM

(71) Applicants: HITACHI, LTD., Tokyo (JP); NATIONAL UNIVERSITY CORPORATION HOKKAIDO UNIVERSITY, Hokkaido (JP)

(72) Inventors: Yusuke Fujii, Tokyo (JP); Ryuya Ando, Tokyo (JP); Manabu Aoki, Tokyo (JP); Kikuo Umegaki, Sapporo (JP); Shinichi Shimizu, Sapporo (JP); Taeko Matsuura, Sapporo (JP); Hiroki Shirato, Sapporo (JP)

(73) Assignees: HITACHI, LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 639 days.

(21) Appl. No.: 17/048,639

(22) PCT Filed: Apr. 11, 2019

(86) PCT No.: PCT/JP2019/015812
§ 371 (c)(1),
(2) Date: Oct. 19, 2020

(87) PCT Pub. No.: WO2019/208243
PCT Pub. Date: Oct. 31, 2019

(65) Prior Publication Data
US 2021/0154495 A1  May 27, 2021

(30) Foreign Application Priority Data
Apr. 27, 2018 (JP) .................... 2018-086846

(51) Int. Cl.
*A61N 5/10* (2006.01)
*A61B 5/055* (2006.01)
(Continued)

(52) U.S. Cl.
CPC ............ *A61N 5/1039* (2013.01); *A61B 5/055* (2013.01); *A61B 6/02* (2013.01); *A61N 5/1049* (2013.01);
(Continued)

(58) Field of Classification Search
CPC .......... A61N 2005/1055; A61N 5/1068; A61N 2005/1089; A61N 5/1081
See application file for complete search history.

(56) References Cited

U.S. PATENT DOCUMENTS

| 6,101,239 A | 8/2000 | Kawasaki et al. |
| 2009/0234219 A1 | 9/2009 | Kruip |

(Continued)

FOREIGN PATENT DOCUMENTS

| EP | 3305200 A1 | 4/2018 |
| EP | 3305366 A1 | 4/2018 |

(Continued)

OTHER PUBLICATIONS

Bradley M. Oborn et al., "Future of medical physics: Real-time MRI-guided proton therapy", Med. Phys. 44(8), Aug. 2017, p. e77-e90.
International Search Report of PCT/JP2019/015812 dated Jun. 26, 2019.

*Primary Examiner* — Colin T. Sakamoto
(74) *Attorney, Agent, or Firm* — MATTINGLY & MALUR, PC

(57) ABSTRACT

A particle therapy system includes an accelerator 1 which generates a particle beam for extraction, an irradiation apparatus 21 which irradiates the particle beam to an irradiation target 26, a gantry 18 which rotates together with the irradiation apparatus 21, and an MRI apparatus 50 which rotates together with the gantry 18. The MRI apparatus 50 includes a magnetic circuit composed of an iron core 60 and a plurality of coils 61 serving as a magnetic flux source. The (Continued)

iron core 60 includes two oppositely disposed magnetic poles 63A and 63B, and a return yoke 64 for connecting the magnetic poles 63A and 63B. The magnetic poles 63A, 63B have cavities 65A, 65B. The particle beam passing through the cavity 65A is irradiated to the irradiation target 26.

<p align="center">12 Claims, 8 Drawing Sheets</p>

(51) Int. Cl.

| | | |
|---|---|---|
| *G01R 33/421* | (2006.01) | |
| *A61B 6/02* | (2006.01) | |
| *G01R 33/38* | (2006.01) | |
| *G01R 33/48* | (2006.01) | |
| *A61B 6/03* | (2006.01) | |
| *A61B 5/00* | (2006.01) | |

(52) U.S. Cl.
CPC ......... *A61N 5/1081* (2013.01); *G01R 33/421* (2013.01); *G01R 33/4215* (2013.01); *A61B 5/0035* (2013.01); *A61B 6/032* (2013.01); *A61N 5/1071* (2013.01); *A61N 2005/1055* (2013.01); *A61N 2005/1061* (2013.01); *A61N 2005/1092* (2013.01); *G01R 33/3806* (2013.01); *G01R 33/4812* (2013.01)

(56) References Cited

U.S. PATENT DOCUMENTS

| | | |
|---|---|---|
| 2018/0098713 A1 | 4/2018 | Forton et al. |
| 2018/0099153 A1 | 4/2018 | Prieels |
| 2018/0099154 A1 | 4/2018 | Prieels |
| 2018/0099155 A1 | 4/2018 | Prieels et al. |
| 2018/0099157 A1 | 4/2018 | Prieels et al. |
| 2018/0099158 A1 | 4/2018 | Brusasco |
| 2018/0099159 A1 | 4/2018 | Forton et al. |
| 2018/0099160 A1 | 4/2018 | Forton |
| 2019/0004131 A1 | 1/2019 | Wachowica et al. |
| 2020/0238102 A1* | 7/2020 | Lamb .................... G16H 20/40 |

FOREIGN PATENT DOCUMENTS

| | | |
|---|---|---|
| EP | 3305367 A1 | 4/2018 |
| EP | 3305368 A1 | 4/2018 |
| EP | 3306334 A1 | 4/2018 |
| EP | 3306335 A1 | 4/2018 |
| EP | 3306336 A1 | 4/2018 |
| EP | 3308834 A1 | 4/2018 |
| JP | 10-192268 A | 7/1998 |
| JP | 2008-543471 A | 12/2008 |
| JP | 2010-012056 A | 1/2010 |
| JP | 2018-61838 A | 4/2018 |

\* cited by examiner

PARTICLE THERAPY SYSTEM

TECHNICAL FIELD

The present invention relates to a particle therapy system configured to irradiate a target volume with a charged particle beam (hereinafter referred to as a particle beam) of, for example, heavy particle such as carbon and helium, and proton.

BACKGROUND ART

As an example of the particle therapy apparatus configured to irradiate the charged particle beam to an irradiation region in a predetermined direction, patent literature 1 discloses the apparatus provided with a charged particle beam source which turns the charged particle beam toward the predetermined direction, and a magnetic field generator which generates the magnetic field in an imaging volume containing the irradiation region simultaneously with irradiation of the charged particle beam. In the disclosure, the magnetic field generator allows entry of the charged particle beam to the irradiation region, and generates a uniform magnetic field in the region to which the charged particle beam is irradiated. The magnetic field is then turned approximately to the predetermined direction.

Non-patent literature 1 discloses the particle therapy system configured to measure the target position using the MRI installed in the gantry rotating around the patient, and execute the gated irradiation for irradiating the particle beam if the target is positioned at a predetermined point (extraction permission range).

CITATION LIST

Patent Literature

Patent Literature 1: Japanese Unexamined Patent Application Publication (Translation of PCT Application) No. 2008-543471

Non-Patent Literature

Non-Patent Literature 1: Bradley M. Oborn et al., "Future of medical physics: Real-time MRI-guided proton therapy", Med. Phys. 44(8) 2017

SUMMARY OF INVENTION

Technical Problem

The process of irradiating a patient, for example, a cancer patient with the particle beam has been known. The particle therapy system configured to irradiate the particle beam includes a charged particle generator, a beam transport system, and a treatment room.

Especially, in the case of the particle therapy system which implements the scanning irradiation process, the particle beam generated and accelerated by the accelerator reaches the irradiation apparatus in the treatment room via the beam transport system. The particle beam is then scanned by the scanning magnet of the irradiation apparatus to form a dose distribution conformal to the target shape inside the patient body.

The respiratory motion of an irradiation target such as the target volume makes it difficult to form the preliminarily planned dose distribution.

The above-described non-patent literature 1 discloses the particle therapy system to implement the process of forming the dose distribution as planned. Specifically, the particle therapy system measures the position of the target using the MRI (Magnetic Resonance Imaging) installed in the gantry that rotates around the patient. If the target is positioned at the predetermined point (extraction permission range), the system executes the gated irradiation for irradiating particle beams.

As for the gantry in which the MRI as disclosed in the non-patent literature 1 is installed, the magnetic line passes in the air outside the MRI. The magnetic field outside the MRI is strengthened. In other words, the leakage magnetic field is enlarged.

Meanwhile, a particle beam monitor for measuring a position and an irradiation dose of the particle beam is susceptible to the magnetic field because of its characteristics. The large magnetic field may cause the problem of difficulty in arrangement of the particle beam monitor close to the patient.

The patent literature 1 discloses the particle therapy system having the MRI with an iron core serving as the magnetic path for returning a magnetic flux in order to avoid the leakage magnetic field.

In the above-structured system, the magnetic flux will return to the iron core so that the equipment susceptible to the magnetic field, for example, the particle beam monitor or the like is easily arrangeable. As the charged particle beam passes across the strong magnetic field, the problem of making the beam orbit susceptible to the electromagnetic force has occurred.

The patent literature 1 discloses the structure for making the direction of the magnetic field generated by the MRI apparatus parallel to the injecting direction of the particle beam for the purpose of avoiding the problem. The structure, however, causes another problem of the complicated structure and enlarged leakage magnetic field.

It is an object of the present invention to provide a simply configured particle therapy system that allows the MRI apparatus to measure the target position, and the particle beam monitor to evaluate the position and the dose of the particle beam with high accuracy.

Solution to Problem

The present invention includes a plurality of elements for solving the above-described problems. An exemplary structure includes an accelerator which generates a charged particle beam for extraction, an irradiation apparatus which irradiates the charged particle beam to an irradiation target, a gantry which rotates together with the irradiation apparatus, and an MRI apparatus which rotates together with the gantry. The MRI apparatus includes a magnetic circuit having an iron core and a plurality of coils serving as a magnetic flux source. The iron core includes two oppositely disposed magnetic poles, and a member for connecting the magnetic poles. At least one of the magnetic poles has a cavity. The charged particle beam passing through the cavity is irradiated to the irradiation target.

Advantageous Effects of Invention

The present invention ensures to provide a simply configured particle therapy system that allows the MRI apparatus to measure the target position, and the particle beam monitor to evaluate the position and the dose of the particle beam with high accuracy. The problems, structures, and effects other than those described above will be clarified by explanations of the examples as described below.

DESCRIPTION OF EMBODIMENT

An example of the particle therapy system according to the present invention will be described with reference to FIGS. 1 to 9.

The particle therapy system according to the example, having an MRI with a return yoke installed in a gantry will be described referring mainly to FIGS. 1 and 2.

Figure 1:
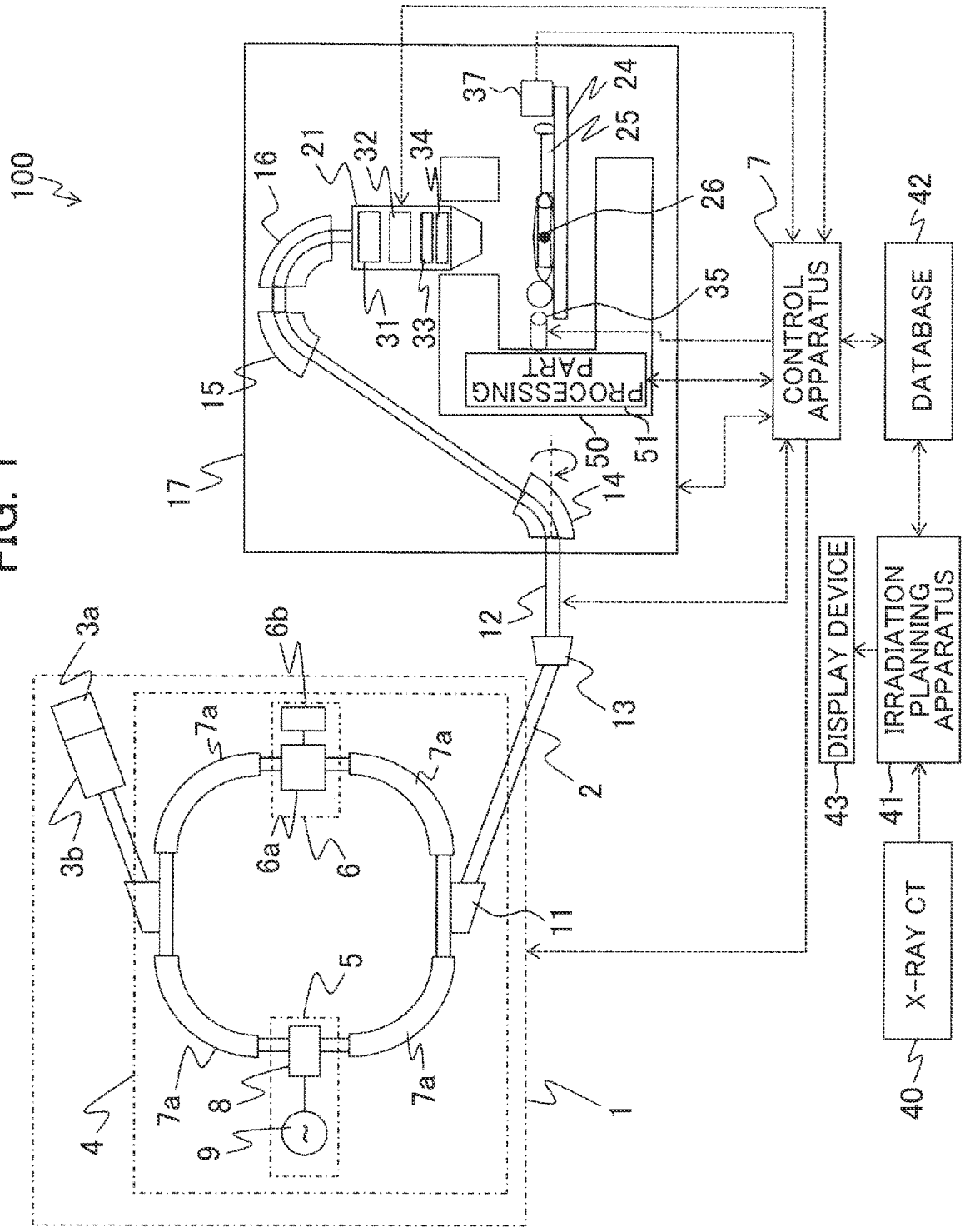
FIG. 1 schematically illustrates an overall structure of a particle therapy system according to the present invention.

Referring to FIG. 1, the particle therapy system of the example includes an accelerator 1, a beam transport system 2, a treatment room 17, and a control apparatus 7.

The accelerator 1 is configured to generate the particle beam for extraction to an irradiation apparatus 21, and includes an ion source 3a, a linac 3b as a preaccelerator, and a synchrotron 4.

The synchrotron 4 includes a bending magnet 7a, a radiofrequency application system 5, and an acceleration system 6.

The bending magnet 7a is disposed on a beam closed orbit of the synchrotron 4. The radiofrequency application system 5 includes an extraction radiofrequency electrode 8 and an extraction radiofrequency power supply 9, which are disposed on the beam closed orbit. The extraction radiofrequency electrode 8 and the extraction radiofrequency power supply 9 are connected by a switch. The acceleration system 6 includes a radiofrequency acceleration cavity 6a formed in the beam closed orbit, and a radiofrequency power supply 6b for applying radiofrequency power to the radiofrequency acceleration cavity 6a. An extraction deflector 11 connects the synchrotron 4 and the beam transport system 2.

The beam transport system 2 includes a beam path 12, a quadrupole magnet, and bending magnets 13, 14, 15, 16. The beam path 12 is connected to the irradiation apparatus 21 disposed in the treatment room 17.

A substantially cylindrical gantry 18 is disposed in the treatment room 17. The gantry 18 is provided with the bending magnets 15, 16 each as a part of the beam transport system 2, the irradiation apparatus 21 for irradiating the particle beam to an irradiation target 26, an MRI apparatus 50, an X-ray generator 35, and an X-ray detector 37. A treatment bed called couch 24 on which an irradiation object 25 is placed is disposed inside the gantry 18.

Figure 2:
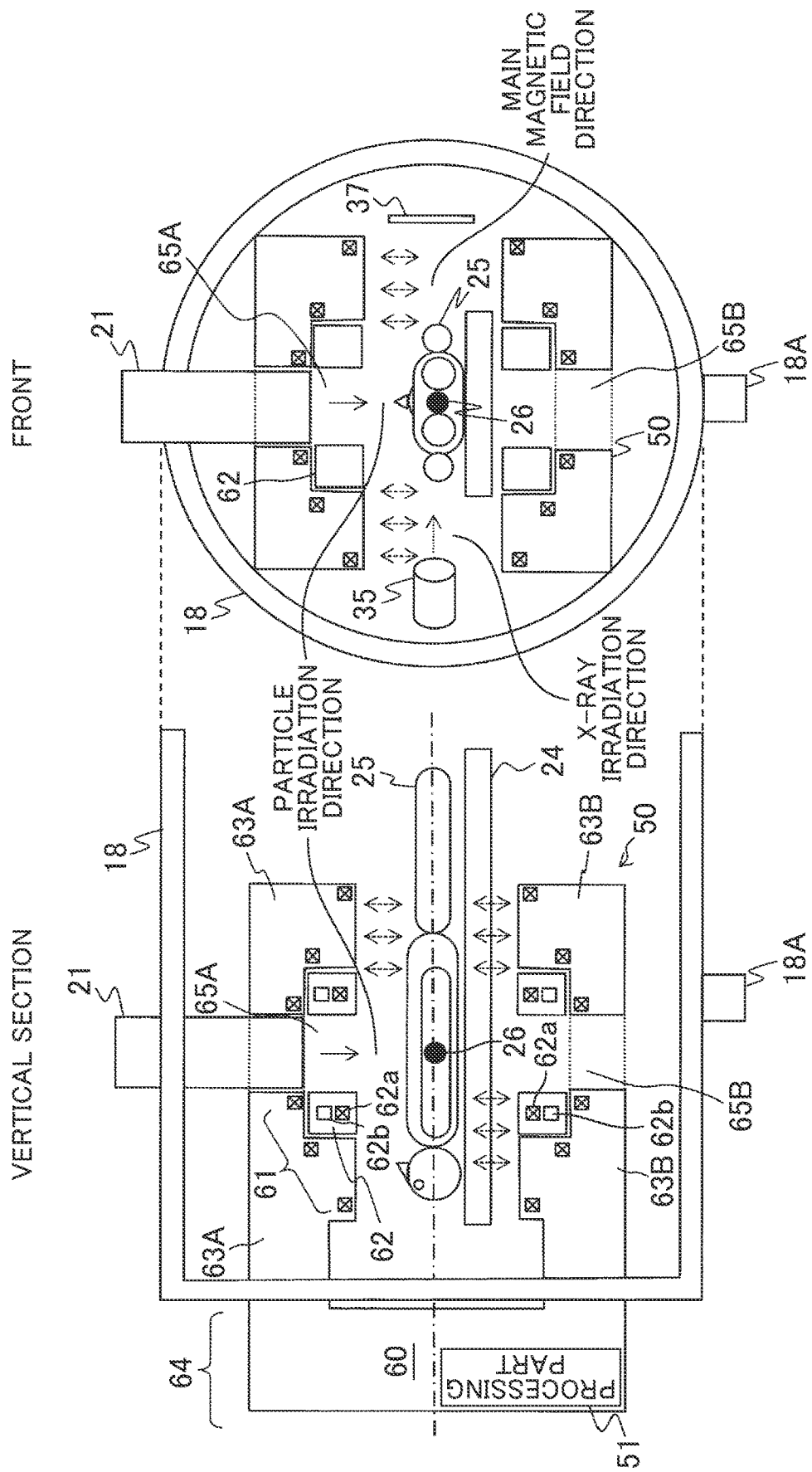
FIG. 2 illustrates an exemplary structure of a treatment room as disclosed in FIG. 1.

As FIG. 2 illustrates, the gantry 18 is made rotatable by a motor 18A. The bending magnets 15, 16, the irradiation apparatus 21, the MRI apparatus 50, the X-ray generator 35, and the X-ray detector 37 are rotated in association with a rotation of the gantry 18. The rotation of the gantry 18, and accompanying rotations of the respective components allows irradiation of the particle beam to the irradiation target 26 of the irradiation object 25 from an arbitrary direction in a plane perpendicular to a rotation axis of the gantry 18.

The irradiation apparatus 21 installed in the gantry 18 includes scanning magnets 31, 32, and a particle beam monitor inside. The particle beam monitor is composed of a position monitor 34 and a dose monitor 33.

The particle therapy system 100 of the example includes the two scanning magnets 31, 32 in the irradiation apparatus 21. The system is configured to change an irradiation position by deflecting the particle beams to two directions (X direction, Y direction), respectively in a plane perpendicular to the beam advancing direction, that is, perform scanning irradiation. The position monitor 34 measures a position of the scanned particle beam and a spread of the particle beam. The dose monitor 33 measures a dose of the irradiated particle beam.

The MRI apparatus 50 is installed in the gantry 18 as shown in FIG. 2. The MRI apparatus 50 includes a passive shield type magnet that allows an iron core 60 to return the magnetic flux generated by a plurality of coils 61 serving as a magnetic flux source, a member 62 that stores a gradient magnetic field coil 62a and a radiofrequency transmission-reception system 62b for causing magnetic resonance phenomena and collecting the resultant signals, and a processing part 51 for controlling energization of the coils 61 and the gradient magnetic field coil 62a, and generating MRI images from detection values of the radiofrequency transmission-reception system 62b so that the MRI images are outputted to the control apparatus 7.

The MRI apparatus 50 of the example is demagnetizable in the following cases: the signal from the MRI apparatus 50 is not used by the control apparatus 7; the MRI apparatus is rotated together with the gantry 18; and the MRI apparatus is retractively moved inside the gantry 18.

The MRI apparatus 50 is disposed to generate the magnetic field in the same direction as that of (parallel to) an axis of the particle beam. The irradiation object 25 is placed so that the irradiation target 26 is within a uniform magnetic field generated by the coils 61 of the MRI apparatus 50. The MRI image of the periphery of the irradiation target 26 is then taken.

The iron core 60 of the MRI apparatus 50 includes two oppositely disposed magnetic poles 63A, 63B, and a return yoke 64 for connecting the magnetic poles 63A and 63B at the far side of the gantry 18. The return yoke 64 and the magnetic poles 63A, 63B constitute a passage route of the magnetic flux, that is, the magnetic circuit.

Each of the magnetic poles 63A, 63B has the same shape, and is made of the same material.

A cavity 65A is formed at the center of the magnetic pole 63A so that the particle beam from the irradiation apparatus 21 passes through the area around the center of the magnetic pole 63A. FIG. 2 illustrates the cavity 65A that is sized to accommodate the irradiation apparatus 21. The cavity 65A of the magnetic pole 63A may be arbitrarily sized to allow at least passage of the scanned beam.

A cavity 65B is formed at the center of the magnetic pole 63B, having the same size and the same shape as those of the cavity 65A formed in the magnetic pole 63A. The magnetic field generated by the coils 61 is strengthened by enhancing symmetry between the upper and the lower magnetic poles 63A and 63B.

FIG. 2 illustrates the system on the assumption that the coils 61 generate the main magnetic flux (magnetostatic field). The source for generating the main magnetic flux is not necessarily limited to the coils 61. It is clearly understood that the main magnetic flux may be generated by a permanent magnet, for example.

As FIG. 2 illustrates, the X-ray generator 35 and the X-ray detector 37 of flat panel type are disposed at both sides of the irradiation object 25, respectively for generating X-rays in a direction perpendicular to the magnetic field generated by the MRI apparatus 50 inside the gantry 18. The X-ray generator 35 generates the X-ray for fluoroscopic imaging. The X-ray detector 37 detects a signal of the X-ray that has been generated by the X-ray generator 35, and passed through the periphery of the irradiation target 26 of the irradiation object 25.

The irradiation target 26 exists inside the irradiation object 25. The irradiated particle beam forms the dose distribution for covering the irradiation target 26 in the irradiation object 25. In the case of the cancer treatment, the irradiation object 25 is a human, and the irradiation target 26 is a tumor.

The control apparatus 7 of the particle therapy system 100 of the example will be described referring to FIG. 1.

The control apparatus 7 is connected to a database 42 as a storage device. The database 42 is connected to an irradiation planning apparatus 41. The irradiation planning apparatus 41 is connected to an X-ray CT 40 and a display device 43. The database 42 stores data (treatment plan) required for irradiation, which have been produced by the irradiation planning apparatus 41.

The control apparatus 7 is connected to the accelerator 1, the beam transport system 2, the gantry 18, the irradiation apparatus 21, the MRI apparatus 50, the X-ray generator 35, and the X-ray detector 37. The control apparatus 7 is configured to control operations of the respective components constituting the accelerator 1, the irradiation apparatus 21, the beam transport system 2, the MRI apparatus 50, the X-ray generator 35, and the X-ray detector 37. The control apparatus 7 outputs each excitation amount of the scanning magnets 31, 32, and receives inputs of detection values from the respective monitors in the irradiation apparatus 21.

Particularly, the control apparatus 7 of the example executes an ON/OFF control of the particle beam irradiation based on the signal of the MRI image periodically acquired from the processing part 51 of the MRI apparatus 50, and executes a moving control of the couch 24 for positioning before irradiation.

During irradiation of the particle beam, for example, it is determined whether or not a three-dimensional position of the irradiation target 26 acquired in real time during irradiation is within a predetermined region. If it is determined that the position is within the region, an extraction radiofrequency application command signal is outputted to the radiofrequency application system 5. If it is determined that the position deviates from the region, the signal is not outputted.

Before irradiation, a difference between the irradiation target 26 and the irradiation position is obtained from the X-ray fluoroscopic image or the MRI image which has been acquired when positioning the irradiation target 26 to the irradiation position as determined in the therapy planning to compute a moving amount of the couch 24. The couch 24 is then transferred.

The control apparatus 7 or the above-described processing part 51 includes one or more processors, a CPU, and the like. Operations of the respective components are controlled through execution of various programs by the control apparatus 7 and the processing part 51. The programs stored in an internal recording medium inside the control apparatus 7, an external recording medium, and the database 42 are read and executed by the CPU.

The process of controlling operations to be executed by the control apparatus 7 and the processing part 51 may be integrated as a single program, separated to form a plurality of programs, or formed as a combination thereof. The program may be partially or entirely implemented by a dedicated hardware, or modulized. The respective programs may be installed in computing machines with the program distribution server and storage media.

Figure 3:
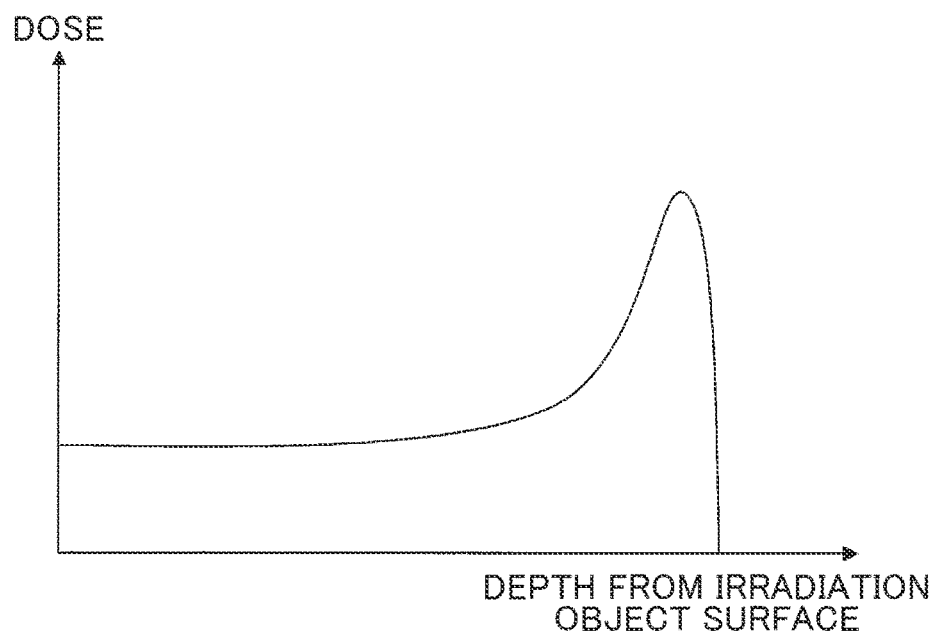
FIG. 3 represents a dose distribution in a depth direction, which has been obtained by irradiating an irradiation object with a single particle beam.
Figure 4:
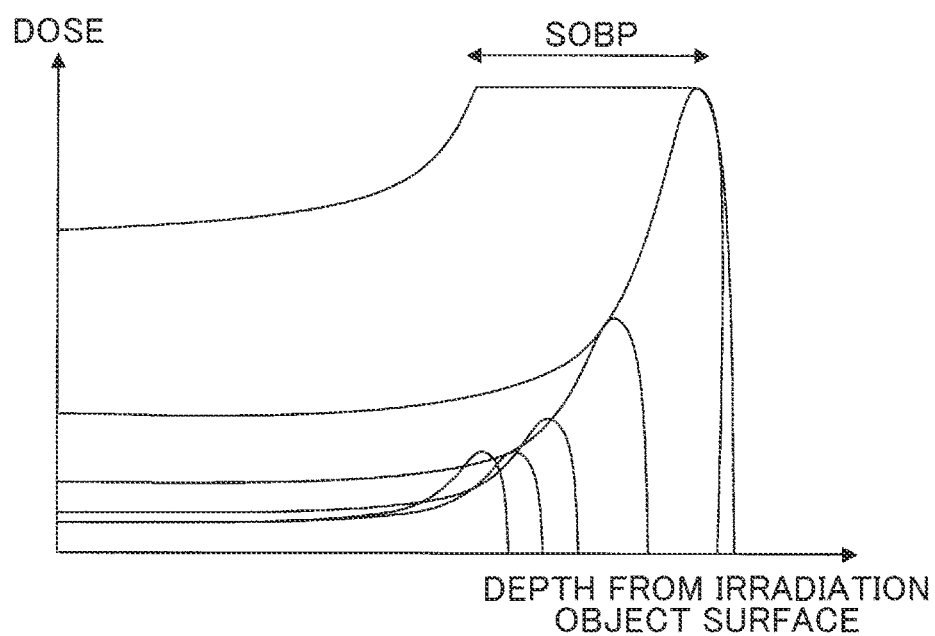
FIG. 4 represents a dose distribution in the depth direction, which has been obtained by irradiating the irradiation object with a plurality of particle beams.

Referring to FIGS. 3 and 4, a relation between the depth of the irradiation target 26 from a surface of the irradiation object 25 in the particle beam system 100 of the example, and the particle beam energy will be described. Each of FIGS. 3 and 4 shows an x-axis indicating the depth of the irradiation target 26, and a y-axis indicating the dose of the particle beam.

FIG. 3 represents the dose distribution formed by the monoenergetic particle beam in the irradiation object as a function of the depth. The peak shown in FIG. 3 is called a Bragg peak. The Bragg peak position depends on the particle beam energy. The Bragg peak position may be adjusted by regulating the particle beam energy. The particle beam by an appropriate dose may be irradiated to the irradiation target 26 at the desired depth.

The irradiation target 26 has a thickness in the depth direction, generating the sharp Bragg peak. The particle beams with various energies are irradiated at an appropriate rate of intensity so that the Bragg peaks are superposed. This may provide a uniform high dose region (SOBP: spread-out Bragg peak) with the same thickness as that of the irradiation target 26 in the depth direction as shown in FIG. 4.

Figure 5:
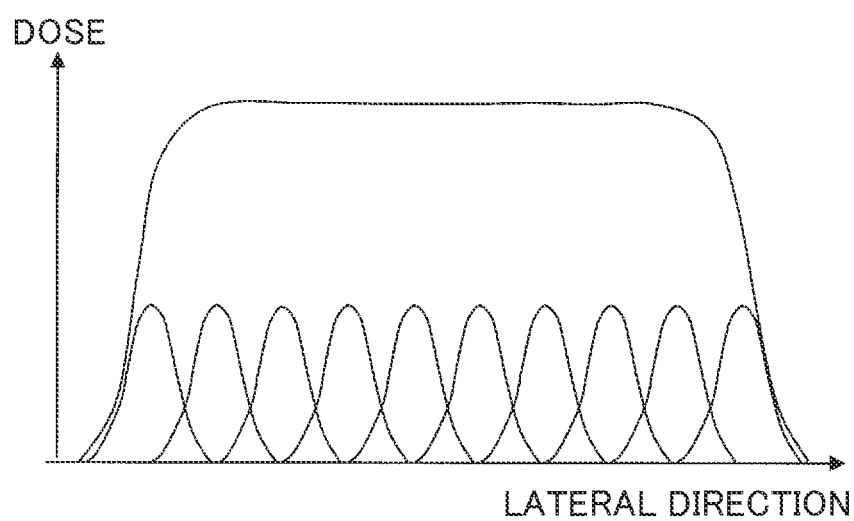
FIG. 5 represents a lateral dose distribution obtained by irradiating the irradiation object with the particle beam.

Referring to FIG. 5, an explanation will be made with respect to a relation between a lateral spread of the irradiation target 26 in the direction perpendicular to the beam axis (direction in XY plane) and the particle beam. FIG. 5 shows an x-axis indicating the lateral spread of the irradiation target 26, and a y-axis indicating the dose at an irradiation spot. The direction perpendicular to the beam axis is called a lateral direction.

After reaching the irradiation apparatus 21, the particle beam is scanned by the two vertically stacked scanning magnets 31, 32 so that the particle beam reaches the desired position in the lateral direction. The lateral spread of the particle beam may be approximated as a Gaussian distribution shape. The Gaussian distributions are arranged at equal intervals, and the distance between the distributions is set to a value substantially equivalent to the standard deviation of the Gaussian distribution. The added distribution, thus has a uniform region as shown in FIG. 5. The dose distribution arranged like the Gaussian distribution is called a spot. The spots as a result of scanning the particle beam are arranged at equal intervals to form laterally uniform dose distribution as shown in FIG. 5.

The lateral beam scanning by the scanning magnets 31, 32, and shifting of the Bragg peak in the depth direction caused by changing the beam energy allow formation of the uniform irradiation field. The irradiation field irradiated with the same energy is laterally spread through scanning of the particle beam by the scanning magnets 31, 32. The unit of the irradiation field is called a "slice".

Before irradiating the irradiation target 26 with the particle beam, the irradiation planning apparatus 41 determines irradiation parameters necessary for irradiation, a gantry angle, and irradiation object position information. The irradiation parameter includes the number N of slices, and N pieces of slice data.

The slice refers to a set of the spots irradiated with the same energy. The slice data include a slice number i, energy Ei, the number $N_i$ of spots, and $N_i$ pieces of spot data. The spot data include a spot number j, an irradiation position $(X_{ij}, Y_{ij})$, and a target irradiation dose $D_{ij}$.

The irradiation parameter is determined in the following manner.

The irradiation object 25 is preliminarily imaged by the X-ray CT 40. The X-ray CT 40 has a function of forming a CT image for each phase of periodic movements of the irradiation target 26. Especially when imaging the patient, the CT image for each respiratory phase may be acquired.

The X-ray CT images the irradiation object, and generates the CT images of the irradiation object 25 corresponding to the n phases. The X-ray CT then transmits the generated CT images to the irradiation planning apparatus 41.

The irradiation planning apparatus 41 displays received image data on a screen of the display device 43. An operator selects a CT image at the reference phase from those at the respective phases. If the target volume is moved by respiration, an expiration phase is selected. The region required to be irradiated for covering the irradiation target 26 is designated on the CT image selected by the operator.

The irradiation planning apparatus 41 obtains and determines a placement position of the irradiation object, the gantry angle, and the irradiation parameters to ensure formation of the dose distribution in the designated region. In other words, the irradiation planning apparatus 41 determines the placement position of the irradiation object and the gantry irradiation angle based on the irradiation object information inputted by the operator, and divides the irradiation target 26 (target volume) into a plurality of slices in the depth direction so that the necessary number N of slices is determined.

When the irradiation object is placed at the irradiation object placement position, the irradiation planning apparatus 41 computes an image to be projected by the X-ray detector 37, and sets the image as the irradiation object position information.

The irradiation planning apparatus 41 obtains the energy Ei of the ion beam suitable for irradiation in accordance with each depth of the respective slices (slice number i). The irradiation planning apparatus 41 determines the number $N_i$ of the irradiation spots for ion beam irradiation, the spot number j, each irradiation position $(X_{ij}, Y_{ij})$ of the respective spots, and each target irradiation dose $D_{ij}$ of the respective spots in accordance with each shape of the slices in consideration of the magnetic field distribution generated by the MRI apparatus 50.

The irradiation planning apparatus 41 obtains the dose distribution formed when irradiating the irradiation object in consideration of the magnetic field of the MRI apparatus 50 in reference to the determined values, and allows the display device 43 to display the obtained dose distribution.

The data are generated by the number of pieces corresponding to the number of the rotation angles of the gantry 18. The generated irradiation parameter, the gantry angle, and the irradiation object position information are transmitted to the database 42, and recorded therein.

As described above, because of the specification, the particle beam monitor (dose monitor 33 and position monitor 34) is susceptible to the magnetic field.

The particle beam monitor includes electrodes of parallel plate type, and voltage is applied across the electrodes. As the particle beam passes through the electrode of the particle beam monitor, gas existing between the parallel plates is ionized. The ionized electrons and ions are moved in an electric field, and collected by the electrodes.

The dose monitor 33 allows one electrode to collect the signal. The position monitor 34 is configured as the electrode divided into a plurality of sections.

When those particle beam monitors are disposed in the magnetic field, the ionized electrons and ions are influenced by the magnetic field to change the path to the electrode. As a result, correction in association with change in the path is required. In the worst case, the electrodes may fail to collect the electrons and ions.

In the example, the use of the return yoke 64 allows reduction in the magnetic field strength around the MRI apparatus 50, and arrangement of the particle beam monitor close to the irradiation object 25. As the monitor becomes closer to the irradiation object 25 for measurement, the position and dose of the particle beam that has reached the irradiation target 26 of the irradiation object 25 may be measured with higher accuracy.

Because of the specification, the X-ray generator 35 is also susceptible to the magnetic field. Specifically, the X-ray generator 35 generates electron beams inside, and causes the electron beams to impinge against the target so that the X-ray is generated. As the orbit of the electron beam is bent under the magnetic field, the electron beam cannot be impinged against the target.

In the example, the use of the return yoke 64 allows reduction in the magnetic field strength around the X-ray generator 35. After positioning using the X-ray generator 35, the magnetic field of the MRI apparatus 50 is excited so that the X-ray image is acquired by the X-ray generator 35 in a non-magnetic field.

In the above-described case, an image of the irradiation target 26 may be taken even in the narrow imaging region. It may be difficult to sufficiently measure the peripheral structure of the irradiation target 26. The X-ray generator 35 allows confirmation of the peripheral structure in the range from the body surface of the irradiation object 25 to the irradiation target 26. This makes it possible to make the MRI apparatus 50 compact.

The MRI apparatus 50 is configured to move toward the far side of the gantry 18 so that it is used only when necessary.

Although the use of the MRI apparatus 50 is beneficial in acquiring the peripheral image of the irradiation target, the irradiation field of the particle beam is restricted by the size of the cavity 65A at the center of the magnetic pole 63A.

When the MRI apparatus 50 is not necessary, the MRI apparatus 50 is retracted to the far side of the gantry 18 in the rotation axis direction. This makes it possible to generate the large irradiation field of the particle beam.

Figure 6:
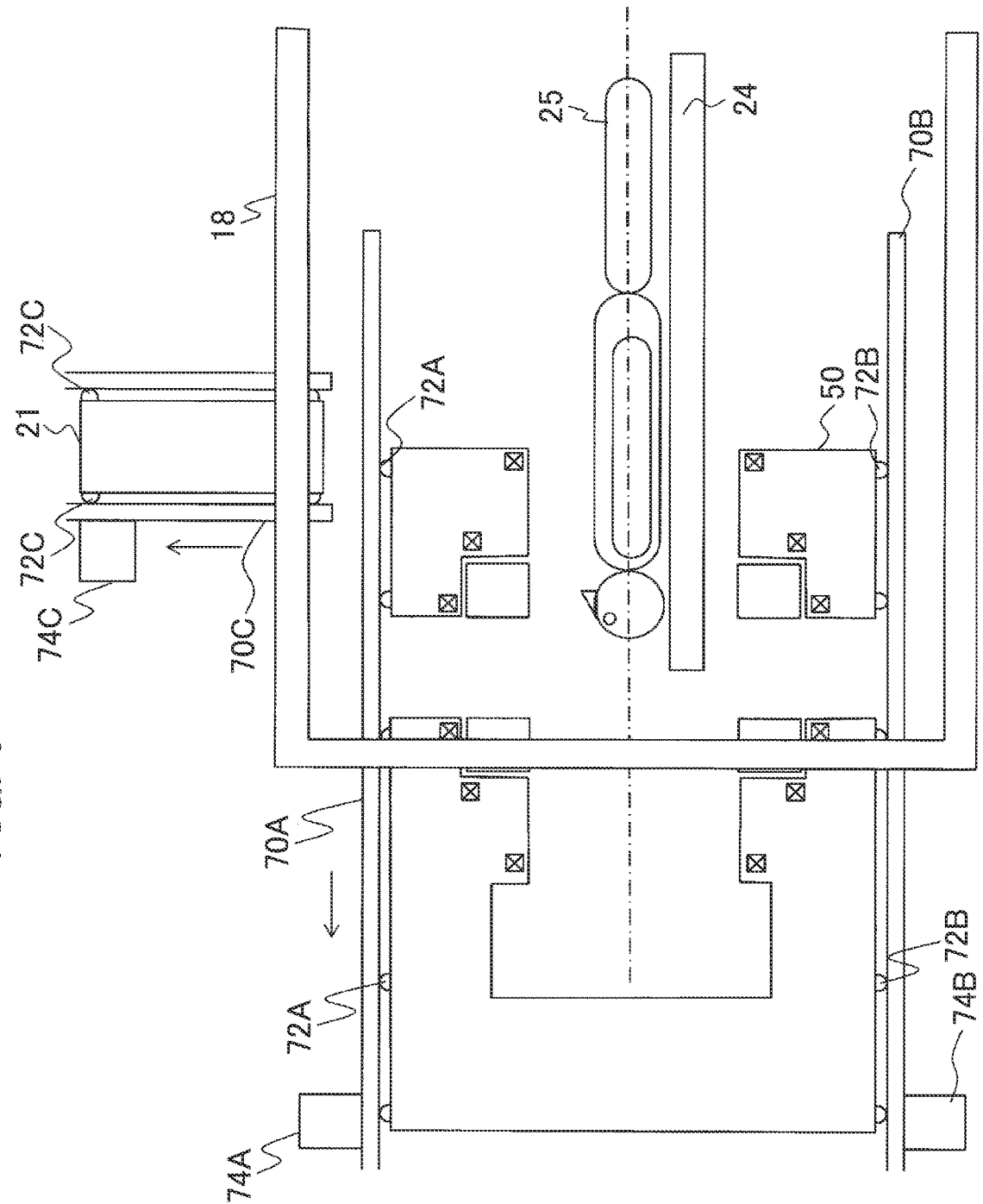
FIG. 6 illustrates a transitional operation for putting an MRI apparatus into a far side of the gantry in the particle therapy system according to the present invention.

An example of the retracting motion will be described referring to FIGS. 6 and 7.

In an irradiation room as shown in FIG. 2, the irradiation apparatus 21 is operated while being partially inserted into the MRI apparatus 50. Referring to FIG. 6, the irradiation apparatus 21 is pulled out of the MRI apparatus 50. The MRI apparatus 50 then is retracted to the far side of the gantry 18.

Figure 7:
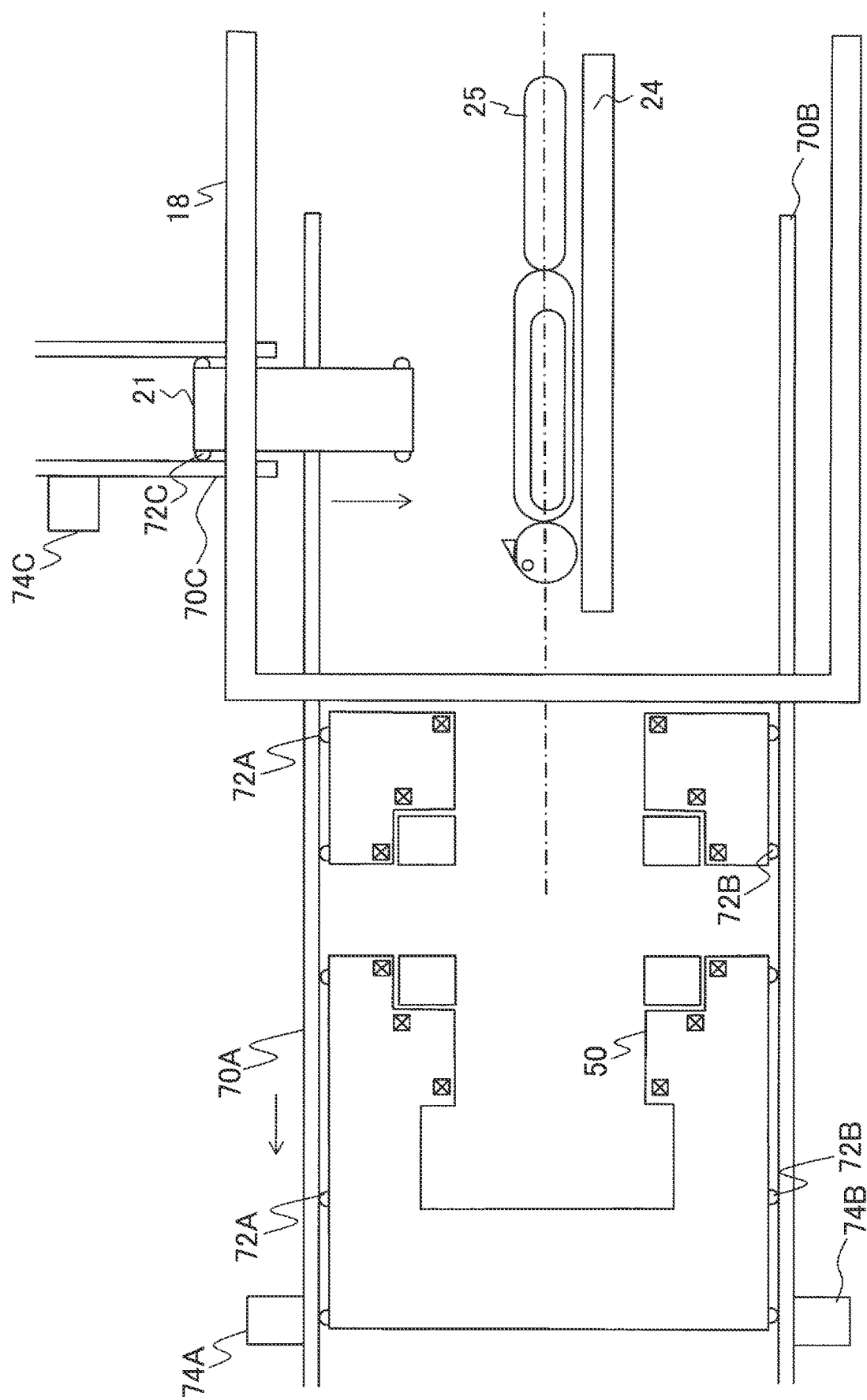
FIG. 7 illustrates a state in which the MRI apparatus has been put into the far side of the gantry in the particle therapy system according to the present invention.

After retracting the MRI apparatus 50 to the far side of the gantry 18, the irradiation apparatus 21 is returned to its original position as shown in FIG. 7. The mechanism and operations as described above remove the MRI apparatus 50 from the gantry 18 when it is not necessary so that the irradiation field of the particle beam is enlarged.

A plurality of wheels 72A, 72B are disposed on outer surfaces of the magnetic poles 63A, 63B of the MRI apparatus 50. The MRI apparatus 50 as illustrated in FIGS. 6 and 7 is retracted with the wheels 72A, 72B driven by motors 74A, 74B while traveling on rails 70A, 70B. The retracting mechanism, however, is not limited to the structure as described above.

The irradiation apparatus 21 is provided with a plurality of wheels 72C to be driven by a motor 74C for retraction while traveling on a rail 70C. The retracting mechanism, however, is not limited to the structure as described above.

As the inside of the irradiation apparatus 21 is in a vacuum state at a position just in front of the particle beam monitor for the purpose of suppressing spread of the particle beam, a vacuum window is provided downstream from the particle beam monitor. The particle beam monitor is capable of irradiating the particle beam with higher accuracy as it becomes closer to the irradiation object. The irradiated particle beam may be thinner as the vacuum region becomes closer to the patient. The thinner the particle beam becomes, the more concentratedly the irradiation target 26 may be irradiated.

Preferably, the particle beam monitor and the vacuum are disposed at the center between the magnetic poles 63A and 63B as close to the irradiation object as possible.

In order to avoid interference upon movement of the MRI apparatus 50 to the far side of the gantry 18, it is preferable to make the vacuum window and the particle beam monitor movable in the beam axis direction of the particle beam.

<Irradiation Procedure>

Figure 8:
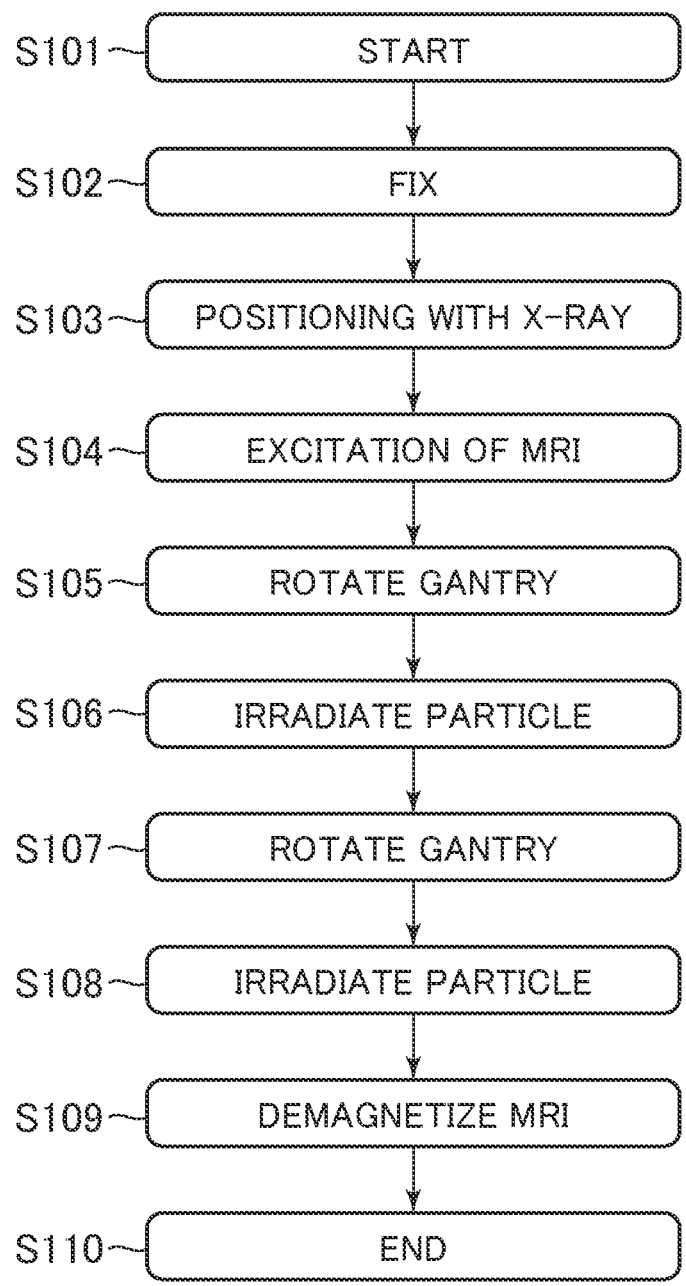
FIG. 8 is a flowchart representing a procedure for irradiating the irradiation object with the particle beam by the particle therapy system according to the present invention.

Assuming that the irradiation object 25 is the patient, an explanation will be made with respect to the procedure for forming the dose distribution to the irradiation target 26 as the target volume using the irradiation parameter, the irradiation object placement information, and the gantry angle, which have been generated by the irradiation planning apparatus 41 referring to FIG. 8. FIG. 8 represents an exemplary case of irradiating the particle beams from two directions.

Referring to FIG. 8, the patient enters into the treatment room 17 so that a course of treatment is started (step S101). The patient then is fixed onto the couch 24 outside the gantry 18 (step S102), and the couch 24 is moved to the inside of the gantry 18.

Positioning is performed using the X-ray generator 35 and the X-ray detector 37 (step S103). In positioning, preferably, the X-ray images in two orthogonally intersecting directions are acquired using the X-ray generator 35. In the process of acquiring the images from two directions, an X-ray image in a horizontal direction is acquired first, and the X-ray image in a perpendicular direction is acquired after rotating the gantry 18 at 90°.

The acquired X-ray images are compared with those of the irradiation object placement information recorded in the database 42. The couch 24 is then moved so that the patient is brought into the planned position.

In the case of a large imaging region, in step S103, it is possible to use the MRI apparatus 50 for positioning instead of using the X-ray by inverting the order of executing steps of S104 and S103.

The X-ray generator 35 and the X-ray detector 37 are rotated at the same rotating speed while having a relative positional relation therebetween kept unchanged to acquire fluoroscopic images from various directions. It is therefore possible to reconstruct the cone-beam CT image from the fluoroscopic images. The cone-beam CT image is compared with the image of the irradiation object placement information to determine the patient placement position. This makes it possible to perform positioning with higher accuracy.

The MRI apparatus 50 is excited (step S104) to rotate the gantry 18 together with the MRI apparatus 50 along the direction for firstly irradiating the particle beam (step S105).

The particle beam is then irradiated (step S106). The flow of irradiating the particle beam will be described later.

When irradiation of the particle beam is finished, the irradiation direction is changed (step S107), and the particle beam is irradiated again (step S108).

When irradiation of the particle beam is finished, the magnetic field of the MRI apparatus 50 is demagnetized (step S109) to pull the couch 24 out of the gantry 18. The patient gets off from the couch 24 to leave the treatment room 17. The irradiation is then finished (step S110).

Operations of the control apparatus 7 during particle beam irradiation executed in steps S106 and S108 will be described referring to FIG. 9.

It is assumed that the operator presses an irradiation preparation start button on a console connected to the control apparatus 7.

Upon recognition of pressing the irradiation preparation start button, the control apparatus 7 receives the irradiation object placement information from the database 42, and prepares each excitation pattern of the electromagnets for extracting the particle beam with designated energy. The irradiation is controlled by setting irradiation parameters, and outputting excited current values obtained from the irradiation position and the energy to a power supply of scanning magnet.

Figure 9:
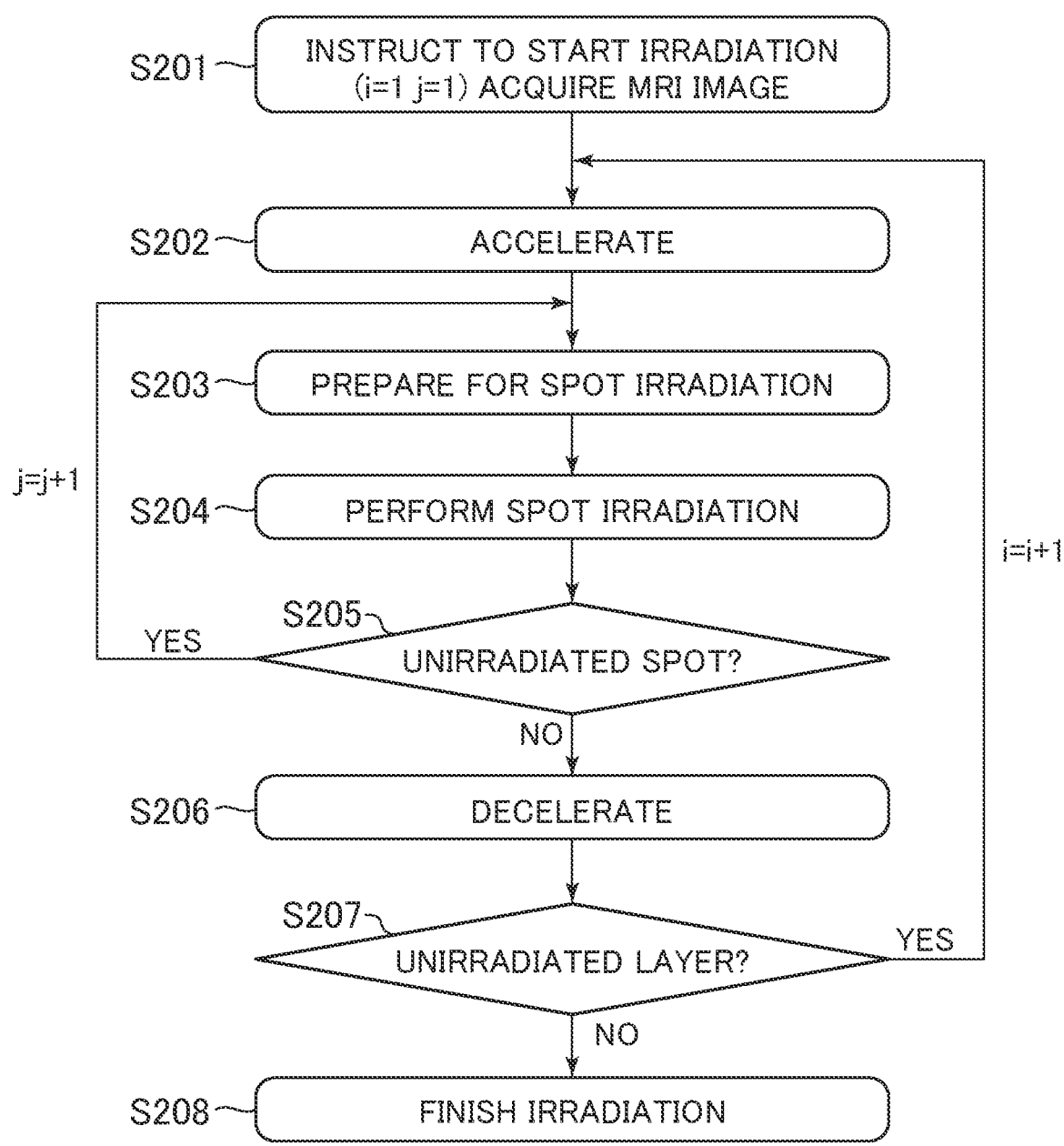
FIG. 9 is a flowchart representing a procedure for controlling irradiation of the particle beam in the particle therapy system according to the present invention.

Referring to FIG. 9, irradiation from the spot with energy number i=1 and the spot number j=1 is started (step S201). Specifically, the control apparatus 7 controls the accelerator 1 to accelerate the particle beam up to energy E1 with the energy number i=1. The control apparatus 7 acquires the MRI images from the MRI apparatus 50 at a fixed cycle, and computes a position (coordinates of target) of the irradiation target 26 from the acquired images.

The control apparatus 7 controls the ion source 3a, the linac 3b, and the synchrotron 4 for acceleration of the particle beam (step S202). Specifically, the particle beam generated by the ion source 3a is introduced into the linac 3b. The linac 3b accelerates the particle beam to bring energy into the state suitable for injection to the synchrotron 4. The particle beam is then injected to the synchrotron 4. The radiofrequency is applied to the particle beam injected to the synchrotron 4 at every passage through the acceleration system 6, and accelerated up to the energy E1 for irradiating the first slice number while rotating along the closed orbit of the synchrotron 4.

The control apparatus 7 prepares for the spot irradiation (step S203). Specifically, the control apparatus 7 controls the power supply of scanning magnet for excitation of the scanning magnets 31, 32 corresponding to the irradiation position of i=1, j=1.

The control apparatus 7 determines whether or not the three-dimensional position of the irradiation target 26, which has been obtained from the MRI image coincides with, or approximates to the position obtained when the irradiation parameters are generated by the irradiation planning apparatus 41. If the positional approximation is determined, the particle beam irradiation is started (S204). If the coincidence or the positional approximation is not determined, the process step S204 is executed again after an elapse of a fixed time period.

Specifically, the control apparatus 7 controls the radiofrequency application system 5 to apply radiofrequency to the particle beam orbiting in the synchrotron 4. The particle beam to which the radiofrequency is applied passes through the extraction deflector 11 and then the beam path 12 to reach the irradiation apparatus 21 inside the treatment room 17. The particle beam is scanned by the scanning magnets 31, 32 inside the irradiation apparatus 21, and passes through the position monitor 34 and the dose monitor 33. Thereafter, the particle beam reaches the inside of the irradiation object 25 for imparting a dose to the irradiation target 26.

The dose of the particle beam which has reached the irradiation target 26 is detected by the dose monitor 33. The control apparatus 7 compares the count of signals from the dose monitor 33 with a target irradiation dose of i=1, j=1 set in the irradiation parameter, and starts operation for stopping extraction when the count reaches the target irradiation dose. Thereafter, the control apparatus 7 controls the radiofrequency application system 5 to interrupt the radiofrequency application so that the extraction is stopped. The control apparatus 7 confirms that the difference between the position measured by the position monitor 34 and the position set in the irradiation parameter is equal to or smaller than a predetermined threshold value.

The control apparatus 7 determines whether or not there is any un-irradiated spot among those of the same slice (step S205). In the case of the spot number j<$N_t$, indicating that there is the un-irradiated spot, the process returns to step S203 for irradiating the (j+1)th spot. On the contrary, if it is determined that all the spots of the same slice have been irradiated, that is, j=$N_t$, the process proceeds to step S206.

The control apparatus 7 decelerates the particle beam (step S206) to bring new particle beams from the linac 3b ready for injection, and kept standby.

The control apparatus 7 determines whether or not there is any un-irradiated layer (step S207). If it is determined that the un-irradiated layer exists, that is, i<N, the control apparatus 7 proceeds the process to step S202 for irradiating the (i+1)th layer. On the other hand, if it is determined that irradiation to all the layers have been finished, that is, i=N, the control apparatus 7 proceeds the process to step S208 for finishing irradiation (step S208).

The irradiation to be performed through the above-described procedure allows irradiation of the particle beams to the irradiation target 26 concentratedly.

Advantageous effects of the example will be described.

The particle therapy system 100 of the example as described above includes the accelerator 1 which generates the particle beam for extraction, the irradiation apparatus 21 which irradiates the particle beam to the irradiation target 26, the gantry 18 which rotates together with the irradiation apparatus 21, and the MRI apparatus 50 which rotates together with the gantry 18. The MRI apparatus 50 includes the magnetic circuit having the iron core 60 and the coils 61 serving as the magnetic flux source. The iron core 60 includes the two oppositely disposed magnetic poles 63A, 63B, and the return yoke 64 for connecting the magnetic poles 63A and 63B. The magnetic poles 63A, 63B have the cavities 65A, 65B, respectively so that the particle beam passes through the cavity 65A for irradiating the irradiation target 26.

As the magnetic line path passes through the inside of the iron core 60, the magnetic field strength may be lowered outside the MRI apparatus 50. This makes it possible to dispose the dose monitor 33 and the position monitor 34 close to the irradiation object 25. The three-dimensional position of the irradiation target 26 may be measured in real time by the MRI apparatus 50 during the particle beam irradiation without employing the complicated structures. It is possible to irradiate the particle beam with high accuracy from an arbitrary angle via the cavity 65A while allowing the particle beam monitor to measure the position and dose of the particle beam with high accuracy.

The structure of the example minimizes the region of the magnetic field caused by the MRI apparatus 50 as small as possible to allow the irradiation planning apparatus 41 to minimize the region for the magnetic field. That is, the influence of the magnetic field caused by the MRI apparatus 50 on the particle beam path has to be considered when the irradiation planning apparatus 41 computes the dose distribution. If the region of the magnetic field is small, the region to be considered for the magnetic field by the irradiation planning apparatus 41 may be minimized. This may shorten the time required for computing the treatment plan, and reduce the memory consumption for computation.

The use of the MRI image allows imaging of the irradiation target 26 during irradiation of the particle beam. This makes it possible to measure the shape of the irradiation target 26 in addition to its position. Capability of measuring change in the shape provides the advantageous effect of highly accurate irradiation of the particle beam.

The use of the image derived from the MRI apparatus 50 allows measurement of change in the irradiation object for each irradiation, for example, change in the body shape of the irradiation object 25. The image taken by the MRI apparatus 50 may be used for executing the adaptive treatment which allows reorganization of the treatment plan using the MRI image. The MRI image may be taken either before or during irradiation of the particle beam.

The control apparatus 7 is provided for executing the ON/OFF control of the particle beam irradiation based on the signal from the MRI apparatus 50. The particle beam may be irradiated to the irradiation target 26 with high accuracy even if the irradiation target 26 is on the move.

As the control apparatus 7 is provided for positional alignment before irradiating the particle beam based on the signal from the MRI apparatus 50, the irradiation target 26 may be positioned to the irradiation position with high accuracy, resulting in further improved accuracy of irradiating the particle beam.

As the advancing direction of the particle beam is parallel to the direction of the magnetic field generated by the MRI apparatus 50, the injecting direction of the particle beam may be made parallel to the magnetic field. Accordingly, the beam orbit may be made insusceptible to the magnetic field, resulting in further improved accuracy in irradiation of the particle beam.

Provision of the X-ray generator 35 which generates X-rays for fluoroscopically imaging the irradiation target 26, and the X-ray detector 37 which detects the X-ray generated by the X-ray generator 35 may make the MRI apparatus 50 further compact as well as the gantry 18. If the MRI apparatus 50 is made compact, the region where the uniform magnetic field generated by the MRI apparatus 50 becomes smaller, and accordingly, the imaging region becomes narrower. It is preferable to use the X-ray generator 35 and the X-ray detector 37 for positioning the couch 24.

A line connecting the X-ray generator 35 and the X-ray detector 37 is made orthogonal to the direction of the magnetic field generated by the MRI apparatus 50. This may reduce the strength of the magnetic field around the X-ray generator 35 susceptible to the magnetic field. The use of the X-ray generator 35 and the X-ray detector 37, thus allows the positional detection of the irradiation target 26 with high accuracy.

The MRI apparatus 50 is excited at a timing after using the X-ray generator 35 so that the X-ray image is acquired by the X-ray generator 35 under no magnetic field.

The MRI apparatus 50 is movable in the direction of the rotation axis of the gantry 18 to allow the single system to generate a large irradiation field of the particle beam, and irradiate the particle beam with high accuracy.

When the signal from the MRI apparatus 50 is not used, or the MRI apparatus 50 moves in the gantry 18, the MRI apparatus 50 may be demagnetized. The MRI apparatus 50 may be excited only at the required timing, and demagnetized while it is unnecessary, resulting in further reduction in susceptibility to the magnetic field.

The oppositely disposed magnetic poles 63A and 63B have the cavities 65A and 65B at the same positions, each having the same shape to enhance a vertically symmetric relation between the magnetic poles 63A and 63B. This allows the coils 61 to generate the magnetic field with high accuracy.

The irradiation apparatus 21 is capable of performing the scanning irradiation to allow highly accurate irradiation of the particle beam to the irradiation target 26.

<Others>

The present invention is not limited to the example as described above, but may be variously modified and applied. The example has been described in detail for readily understanding of the present invention which is not necessarily limited to the one provided with all structures as described above.

In the structure of the example as described above, an explanation has been made that the direction in which the particle beam is irradiated is parallel to the direction of the main magnetic field generated by the MRI apparatus 50 (oriented in the same direction). The two directions, however, do not have to be strictly parallel to each other. That is, deviation from parallelism by +/−10° is permissible. Those directions do not have to be necessarily parallel to each other. The example may be implemented by the system in which the directions are either orthogonal, nonorthogonal or nonparallel to each other.

An examination has also been made that the line connecting the X-ray generator 35 and the X-ray detector 37 is orthogonal to the particle irradiation direction. The two directions do not have to be strictly orthogonal to each other. That is, deviation from 90° by +/−10° is permissible. Those directions do not have to be necessarily orthogonal to each other. The example may be implemented by the system in which the directions are parallel to each other.

In the example, the return yoke 64 of the iron core 60 is disposed at the far side of the gantry 18. However, such arrangement of the components is not necessarily limited to the example as described above.

The return yoke 64 may be disposed on the floor surface or the ceiling surface of the gantry 18. The beam injecting direction and the space for the X-ray generator may be re-arranged in accordance with the modification of the structure according to the present invention.

An explanation has been made with respect to the use of the scanning magnets 31, 32 for executing the irradiation process of scanning type. The present invention is applicable to another technique for irradiation such as the wobbler method and the double scattering method for forming the dose distribution conformal to the shape of the irradiation target 26 using the collimeter and the bolus after spreading the particle beam distribution.

An explanation has been made with respect to the gated irradiation process for irradiating the particle beam only when the irradiation target 26 reaches the target position. The present invention is applicable to the tracking irradiation process for changing the excitation amount of the scanning magnet in accordance with the position of the irradiation target 26. It is also possible to combine the gated irradiation process with the tracking irradiation process.

In the example, an explanation has been made with respect to the spot scanning for stopping extraction of the particle beam for each spot as an exemplary case. However, the present invention is applicable to the raster scanning method and the line scanning irradiation method in which extraction of the particle beam is not stopped.

The explanation has been made with respect to the direct detection of the irradiation target 26 by the MRI apparatus 50. It is possible to indirectly detect the position of the irradiation target 26 by detecting a substance near the irradiation target 26, or a preliminarily embedded fiducial marker as a substitute of the irradiation target 26.

An explanation has been with respect to the use of the synchrotron as the accelerator. The accelerator of other type such as the cyclotron and the synchrocyclotron may be used. In the case of using the cyclotron, the beam is extracted from the cyclotron toward the beam transport system.

The particle beam may be directly transported from the accelerator to the irradiation apparatus without the beam transport system.

LIST OF REFERENCE SIGNS 1 accelerator
7 control apparatus
17 treatment room
18 gantry
18A motor
21 irradiation apparatus
24 couch
25 irradiation object
26 irradiation target
31, 32 scanning magnet
33 dose monitor
34 position monitor
35 X-ray generator
37 X-ray detector
40 X-ray CT
41 irradiation planning apparatus
42 database
50 MRI apparatus
51 processing part
60 iron core
61 coil
62 member
62a gradient magnetic field coil
62b radiofrequency transmission-reception system
63A, 63B magnetic pole
64 return yoke (member)

65A, 65B cavity
70A, 70B, 70C rail
72A, 72B, 72C wheel
74A, 74B, 74C motor
100 particle therapy system

The invention claimed is:

1. A particle therapy system, comprising:
an accelerator which generates a charged particle beam for extraction;
an irradiation apparatus which irradiates the charged particle beam to an irradiation target;
a gantry which rotates together with the irradiation apparatus; and
an MRI apparatus which rotates together with the gantry,
wherein the MRI apparatus includes a magnetic circuit having an iron core and a plurality of coils serving as a magnetic flux source,
wherein the iron core includes two oppositely disposed magnetic poles, and a member for connecting the magnetic poles, and
wherein the MRI apparatus is movable to a direction of a rotation axis of the gantry.

2. A particle therapy system, comprising:
an accelerator which generates a charged particle beam for extraction;
an irradiation apparatus which irradiates the charged particle beam to an irradiation target;
a gantry which rotates together with the irradiation apparatus; and
an MRI apparatus which rotates together with the gantry,
wherein the MRI apparatus includes a magnetic circuit having an iron core and a plurality of coils serving as a magnetic flux source,
wherein the iron core includes two oppositely disposed magnetic poles, and a member for connecting the magnetic poles,
wherein at least one of the magnetic poles has a cavity,
wherein the charged particle beam passing through the cavity is irradiated to the irradiation target, and
wherein the MRI apparatus is movable to a direction of a rotation axis of the gantry.

3. The particle therapy system according to claim 1, further comprising:
a control apparatus which executes an ON/OFF control of irradiating the charged particle beam based on a signal from the MRI apparatus.

4. The particle therapy system according to claim 1, further comprising:
a control apparatus for positioning of the charged particle beam before irradiation based on a signal from the MRI apparatus.

5. The particle therapy system according to claim 1,
wherein an advancing direction of the charged particle beam is parallel to a direction of a magnetic field generated by the MRI apparatus.

6. The particle therapy system according to claim 1, further comprising:
an X-ray generator which generates X-rays for fluoroscopic imaging of the irradiation target, and an X-ray detector which detects the X-ray generated by the X-ray generator.

7. The particle therapy system according to claim 5,
wherein a line for connecting the X-ray generator and the X-ray detector is orthogonal to a direction of a magnetic field generated by the MRI apparatus.

8. The particle therapy system according to claim 5,
wherein the MRI apparatus is excited at a timing after using the X-ray generator.

9. The particle therapy system according to claim 1,
wherein the MRI apparatus is demagnetizable when a signal from the MRI apparatus is not used, or the MRI apparatus is moved in the gantry.

10. The particle therapy system according to claim 1,
wherein the oppositely disposed magnetic poles have the cavities each with the same shape at the same position.

11. The particle therapy system according to claim 1,
wherein the accelerator is any one of a synchrotron, a cyclotron, and a synchrocyclotron.

12. The particle therapy system according to claim 1,
wherein the irradiation apparatus is capable of executing a scanning irradiation process.

* * * * *